US012636293B2

(12) United States Patent
Scaduto

(10) Patent No.: US 12,636,293 B2
(45) Date of Patent: May 26, 2026

(54) METHODS OF TREATING CHARCOT-MARIE-TOOTH DISEASE

(71) Applicant: CMTx Biotech Inc., Kings Park, NY (US)

(72) Inventor: Joseph Scaduto, Kings Park, NY (US)

(73) Assignee: CMTx Biotech Inc., Kings Park, NY (US)

( * ) Notice: Subject to any disclaimer, the term of this patent is extended or adjusted under 35 U.S.C. 154(b) by 1209 days.

(21) Appl. No.: 17/601,258

(22) PCT Filed: Apr. 3, 2020

(86) PCT No.: PCT/US2020/026670

§ 371 (c)(1),
(2) Date: Oct. 4, 2021

(87) PCT Pub. No.: WO2020/206321

PCT Pub. Date: Oct. 8, 2020

(65) Prior Publication Data

US 2022/0175803 A1 Jun. 9, 2022

Related U.S. Application Data

(60) Provisional application No. 62/829,393, filed on Apr. 4, 2019.

(51) Int. Cl.
*A61K 31/65* (2006.01)
*A61P 25/02* (2006.01)

(52) U.S. Cl.
CPC .............. *A61K 31/65* (2013.01); *A61P 25/02* (2018.01)

(58) Field of Classification Search
CPC ................................ A61K 31/65; A61P 25/02
See application file for complete search history.

(56) References Cited

U.S. PATENT DOCUMENTS

| | | | | |
|---|---|---|---|---|
| 7,459,531 | B2 | 12/2008 | Moore et al. | |
| 9,688,679 | B2 | 6/2017 | Stogniew et al. | |
| 9,845,324 | B2 | 12/2017 | Allen et al. | |
| 10,045,992 | B2 | 8/2018 | Stogniew et al. | |
| 10,245,992 | B2 | 4/2019 | Garrison et al. | |
| 2002/0042372 | A1 | 4/2002 | Olsen et al. | |
| 2003/0027776 | A1 | 2/2003 | Roschke | |
| 2003/0203881 | A1* | 10/2003 | Duncan | A61K 45/06 514/152 |
| 2004/0063674 | A1 | 4/2004 | Levy et al. | |
| 2004/0198658 | A1 | 10/2004 | Olsen et al. | |
| 2005/0208565 | A1 | 9/2005 | Roschke | |
| 2007/0015738 | A1 | 1/2007 | Walker et al. | |
| 2007/0190149 | A1 | 8/2007 | Zahos | |
| 2007/0292403 | A1 | 12/2007 | Nivaggioli | |
| 2008/0003208 | A1 | 1/2008 | Nivaggioli | |
| 2008/0221132 | A1 | 9/2008 | Cai et al. | |
| 2009/0098221 | A1* | 4/2009 | Nivaggioli | A61K 31/6615 514/99 |
| 2010/0254944 | A1 | 10/2010 | Subramanian et al. | |
| 2011/0008306 | A1 | 1/2011 | Nivaggioli | |
| 2015/0174144 | A1* | 6/2015 | Bowser | A61K 31/65 514/152 |
| 2018/0127370 | A1 | 5/2018 | O'Neill et al. | |
| 2018/0221375 | A1 | 8/2018 | Allen et al. | |

FOREIGN PATENT DOCUMENTS

| | | | | |
|---|---|---|---|---|
| WO | 01/66657 | A3 | 9/2001 | |
| WO | 2007075269 | A2 | 7/2007 | |
| WO | WO-2007133673 | A2 * | 11/2007 | A61K 31/7004 |
| WO | 2008137137 | A1 | 11/2008 | |
| WO | 2014012094 | A2 | 1/2014 | |
| WO | 2015073109 | A1 | 5/2015 | |
| WO | 2018089433 | A1 | 5/2018 | |
| WO | 2018089493 | A1 | 5/2018 | |
| WO | 2018191146 | A1 | 10/2018 | |

OTHER PUBLICATIONS

Hayashi, M., Abe, A., Murakami, T. et al. Molecular analysis of the genes causing recessive demyelinating Charcot-Marie-Tooth disease in Japan. J Hum Genet 58, 273-278 (2013). https://doi.org/10.1038/jhg.2013.1 (Year: 2013).*
Perea et al., Hum Mol Genet. May 1, 2001;10(10):1007-18 (Year: 2001).*
Michael O. Griffin, Guillermo Ceballos, Francisco J. Villarreal, Pharmacological Research, vol. 63, Issue 2,2011, pp. 102-107. (Year: 2011).*
Perea, Javier, et al. "Induced Myelination and Demyelination in a Conditional Mouse Model of Charcot-Marie-Tooth Disease Type 1A," Human Molecular Genetics, vol. 10, No. 10, pp. 1007-1018 (2001).
Griffin, Michael O., et al., "Tetracycline Compounds with Non-Antimicrobial Organ Protective Properties: Possible Mechanisms of Action," Pharmacological Research, vol. 63, No. 2, pp. 102-107 (2011).
Agnihotri, Rupali, et al., "Chemically Modified Tetracyclines: Novel Therapeutic Agents in the Management of Chronic Periodontitis," Indian Journal of Pharmacology, vol. 44, No. 2, pp. 161-167 (2012).
Eighth Meeting and the 10th Anniversary of the European Neurological Society. J Neurol, vol. 245, pp. 335-494 (1998). https://doi.org/10.1007/s004150050232.
El-Abassi, et al., "Charcot-Marie-Tooth Disease: An Overview of Genotypes, Phenotypes, and Clinical Management Strategies," PM&R, vol. 6, No. 4, pp. 342-355 (2014). (Abstract Only).

* cited by examiner

*Primary Examiner* — Clinton A Brooks
*Assistant Examiner* — Izabela Schmidt
(74) *Attorney, Agent, or Firm* — Hoffmann & Baron LLP

(57) ABSTRACT

A method of treating Charcot Marie Tooth Disease in a human in need thereof. The method comprises systemically administering to the human a non-antibacterial tetracycline compound or antibacterial tetracycline compound, in an amount that is effective to treat Charcot Marie Tooth Disease but has substantially no antibacterial activity.

18 Claims, No Drawings

METHODS OF TREATING CHARCOT-MARIE-TOOTH DISEASE

This application is a U.S. National Phase of, and Applicant claims priority from, International Patent Application No. PCT/US2020/026670, filed Apr. 3, 2020, which claims priority from U.S. Provisional Application Ser. No. 62/829,393, filed Apr. 4, 2019, each of which is incorporated herein by reference in its entirety.

BACKGROUND OF THE INVENTION

Peripheral neuropathies are among the most common inherited neurological disorders. Of the peripheral neuropathies, Charcot-Marie-Tooth Disease (CMTD) is the most common with a prevalence of 1 in 2500 (Jerath et al., "Hereditary motor and sensory neuropathies: Understanding molecular pathogenesis could lead to future treatments strategies." *Biochim. Biophys. Acta.* 1852(4):667-78 (2015)). Charcot-Marie-Tooth Disease is named after three neurologists who described the condition in 1886. Since CMTD affects approximately 2.8M people worldwide (and less than 200,000 patients in the U.S.), it is considered an orphan disease indication (Miller et al., "Strategy for genetic testing in Charcot-Marie disease." Acta. Myol. 30(2):109-16 (2011)).

Charcot-Marie-Tooth Disease is characterized by progressive loss of muscle tissue and touch sensation, and most forms show clinical commonalities such as progressive distal muscle weakness, muscular atrophy, and sensory dysfunction, mostly being downstream features of axonal degeneration. Patients experience motor nerve degeneration resulting in muscle weakness and atrophy in the extremities, as well as degeneration of sensory nerves resulting in a reduced ability to feel heat, cold, and pain. Charcot-Marie-Tooth patients typically display foot deformities, decreased reflexes, and bilateral foot drop.

About 78 subtypes of CMTD have been identified and extensively studied in effort to understand biological pathways. Next generation molecular sequencing has improved the diagnosis as well as the understanding of CMTD. However, current disease management simply includes physical therapy, occupational therapy, braces and other orthopedic devices, and orthopedic surgery. Pain-killing drugs can also be prescribed for individuals who have severe pain, but are not disease-modifying.

Thus, there remains a critical unmet need for the development and regulatory approval of innovative, safe and efficacious therapies for the treatment and control of Charcot-Marie-Tooth Disease.

SUMMARY OF THE INVENTION

The present invention provides methods of treating Charcot-Marie-Tooth Disease (CMTD) in a human in need thereof.

In one embodiment, the method comprises systemically administering to the human a non-antibacterial tetracycline compound in an amount that is effective to treat CMTD. Examples of non-antibacterial tetracycline compounds include 6-demethyl-6-deoxy-4-dedimethylaminotetracycline (CMT-3); 4-dedimethylaminodoxycycline (CMT-8); 9-amino-6-demethyl-6-deoxy-4-dedimethylaminotetracycline (CMT-308); 4-de(dimethylamino)-minocycline (CMT-10), and salts thereof.

In one embodiment, the non-antibacterial tetracycline compound is administered in an amount that results in a plasma concentration which is about 0.01 μg/ml to about 1 μg/ml. In one embodiment, the non-antibacterial tetracycline compound is administered at a daily dose of about 10 mg/kg/day to about 100 mg/kg/day. In one embodiment, the non-antibacterial tetracycline compound is administered at a daily dose of about 1 mg/kg/day to about 20 mg/kg/day. In one embodiment, the non-antibacterial tetracycline compound is administered by controlled release over a 24 hour period.

In one embodiment, CMT-3 is administered in an amount that results in a plasma concentration which is up to about 1.0 μg/ml. In one embodiment, CMT-3 is administered at a daily dose of up to about 1 to 20 mg/day.

In one embodiment, the method comprises administering systemically to the human an antibacterial tetracycline compound in an amount that is effective to treat CMTD, but has substantially no antibacterial activity. Examples of antibacterial tetracycline compounds include doxycycline, minocycline, tetracycline, oxytetracycline, chlortetracycline, demeclocycline, lymecycline and pharmaceutically acceptable salts thereof.

In one embodiment, the antibacterial tetracycline compound is administered in an amount that results in a plasma concentration which is less than approximately 80%, 75%, 70%, 65%, 60%, 55%, 50%, 45%, 40%, 35%, 30%, 25%, 20%, 15%, 10%, 5%, 1% or 0.5% of MIC of the tetracycline compound for commonly-occurring bacteria.

In one embodiment, the antibacterial tetracycline compound is administered in an amount which is less than approximately 80%, 75%, 70%, 65%, 60%, 55%, 50%, 45%, 40%, 35%, 30%, 25%, 20%, 15%, 10%, 5%, 1% or 0.5% of the minimum antibacterial dose.

In one embodiment, the tetracycline compound is doxycycline administered in a daily amount of from about 10 to about 60 milligrams. In one embodiment, the doxycycline is administered twice a day in a dose of about 20 mg. In one embodiment, the doxycycline is administered by controlled release over a 24 hour period, typically in an amount of about 40 mg. In one embodiment, doxycycline administered in an amount which results in a plasma concentration in the range of about 0.1 to about 0.8 μg/ml.

In one embodiment, the systemic administration of tetracycline compounds is oral administration, intravenous injection, intramuscular injection, subcutaneous administration, transdermal administration or intranasal administration.

DETAILED DESCRIPTION OF THE INVENTION

The present invention is directed to methods, and pharmaceutical compositions, to treat Charcot-Marie-Tooth disease (CMTD) in human subjects in need thereof.

The methods include the administration of particular pharmaceutical compositions to a human subject, in need thereof, in an amount which is effective to treat CMTD. A human subject in need thereof is a human who suffers from the symptoms of, and/or has been diagnosed as having, CMTD. Administration includes administration by a physician or self-administration.

Charcot-Marie-Tooth Disease is an inherited peripheral neuropathy which is classified into about 78 subtypes based on the pattern of inheritance and the electrophysiology, e.g., autosomal dominant (AD) demyelinating (CMT1); AD axonal (CMT2); and autosomal recessive and X-linked (CMTX) subtypes.

The pharmaceutical compositions of the present invention comprise tetracycline compounds. Tetracycline compounds include non-antimicrobial (e.g., non-antibacterial) tetracycline compounds, and antimicrobial (e.g., antibacterial) tetracycline compounds.

The tetracyclines are a class of compounds of which tetracycline is the parent compound. Tetracycline has the following general structure:

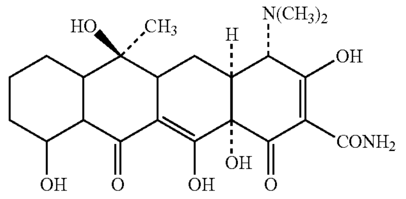 [SMILES: CN(C)[C@@H]1C(O)=C(C(N)=O)C(=O)[C@@]2(O)C(O)=C3C(=O)C4C(O)CCCC4[C@@](C)(O)C3C[C@@H]12]

The numbering system of the multiple ring nucleus is as follows:

Structure B

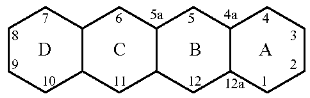

Tetracycline, as well as the oxytetracycline and chlorotetracycline derivatives, exists in nature, and are all well-known antibacterial compounds. Semisynthetic derivatives such as 7-dimethylaminotetracycline (minocycline) and 6α-deoxy-5-hydroxytetracycline (doxycycline) are also known tetracycline antibacterial compounds. Natural tetracyclines may be modified without losing their antibacterial properties, although certain elements of the structure must be retained to do so.

Some examples of antibacterial (i.e., antimicrobial) tetracycline compounds include doxycycline, minocycline, tetracycline, oxytetracycline, chlortetracycline, demeclocycline, lymecycline and their pharmaceutically acceptable salts.

Non-antimicrobial (e.g., non-antibacterial) tetracycline compounds are structurally related to the antibacterial tetracyclines, but have had their antibacterial activity substantially or completely eliminated by chemical modification. For example, non-antibacterial tetracycline compounds are at least about ten times, preferably at least about twenty five times, less antibacterial than doxycycline. In other words, non-antibacterial tetracycline compounds are incapable of achieving antibacterial activity comparable to that of doxycycline at concentrations at least about ten times, preferably at least about twenty five times, greater than that of doxycycline.

Examples of chemically modified non-antimicrobial (e.g., non-antibacterial) tetracyclines (i.e., CMTs) suitable for the methods of the present invention include tetracycline compounds which lack the 4-dimethyl(amino) group. Examples of such non-antibacterial compounds include: 4-de(dimethylamino)tetracycline (CMT-1), tetracyclinonitrile (CMT-2), 6-demethyl-6-deoxy-4-de(dimethylamino)tetracycline (CMT-3), 7-chloro-4-de(dimethylamino)tetracycline (CMT-4), tetracycline pyrazole (CMT-5), 4-hydroxy-4-de(dimethylamino)tetracycline (CMT-6), 4-de(dimethylamino-12α-deoxytetracycline (CMT-7), 6-deoxy-5-hydroxy-4-de (dimethylamino)tetracycline (CMT-8), 4-de (dimethylamino)-12α-deoxyanhydrotetracycline (CMT-9), and 4-de(dimethylamino)-minocycline (CMT-10). Further examples of suitable compounds are recited in Table 1. Still further examples of suitable tetracycline compounds include any non-antimicrobial tetracycline derivative disclosed generically or specifically in U.S. Pat. No. 6,638,922, which are herein incorporated by reference.

Examples of CMTs particularly suited for the present invention include 6-demethyl-6-deoxy-4-de(dimethylamino)tetracycline (CMT-3); 9-amino-6-demethyl-6-deoxy-4-dedimethylaminotetracycline (CMT-308); 6-deoxy-5-hydroxy-4-de(dimethylamino)tetracycline (CMT-8); and 4-de (dimethylamino)-minocycline (CMT-10).

In some embodiments, the tetracycline compounds which have a low phototoxicity are used in the present invention, or are administered in an amount that results in a plasma level at which the phototoxicity is acceptable. Phototoxicity is a chemically-induced photosensitivity. Such photosensitivity renders skin susceptible to damage, e.g., sunburn, blisters, accelerated aging, erythemas and eczematoid lesions, upon exposure to light, in particular ultraviolet light. The preferred amount of the tetracycline compound produces no more phototoxicity than is produced by the administration of a 40 mg total daily dose of doxycycline.

Examples of tetracycline compounds with low phototoxicity include, but are not limited to, tetracycline compounds having general formulae:

Structure K

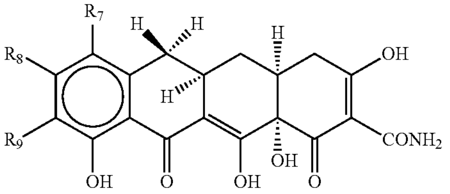

wherein: R7, R8, and R9 taken together in each case, have the following meanings:

| R7 | R8 | R9 | |
|---|---|---|---|
| hydrogen | hydrogen | amino | (CMT-308) |
| hydrogen | hydrogen | palmitamide | (CMT-311) |
| hydrogen | hydrogen | dimethylamino | (CMT-306) |

and

Structure L

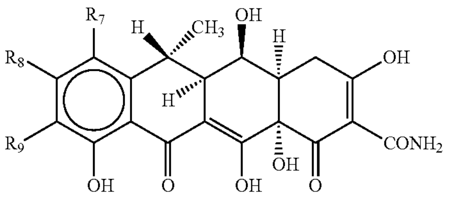

Structure M

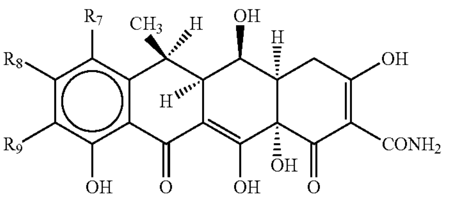

-continued

Structure N

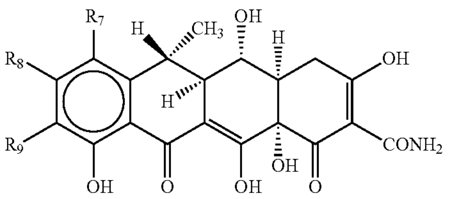

Structure O

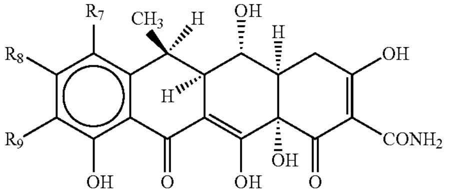

wherein: R7, R8, and R9 taken together in each case, have the following meanings:

| R7 | R8 | R9 | |
|---|---|---|---|
| hydrogen | hydrogen | hydrogen | (CMT-8) |
| hydrogen | hydrogen | acetamido | (CMT-801) |
| hydrogen | hydrogen | dimethylaminoacetamido | (CMT-802) |
| hydrogen | hydrogen | palmitamide | (CMT-803) |
| hydrogen | hydrogen | nitro | (CMT-804) |
| hydrogen | hydrogen | amino | (CMT-805) |

and

Structure P

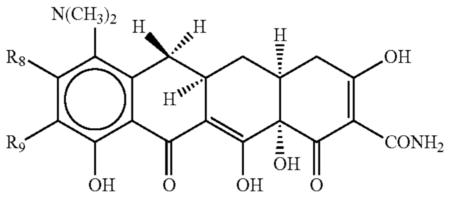

wherein: R8, and R9 taken together are, respectively, hydrogen and nitro (CMT-1002).

Throughout this specification, quantities are defined by ranges, and by lower and upper boundaries of ranges. Each lower boundary can be combined with each upper boundary to define a range. The lower and upper boundaries should each be taken as a separate element.

According to the present invention, a tetracycline compound is administered in any amount that results in a tetracycline plasma concentration which is effective to treat CMTD but which has no antimicrobial (e.g., no antibacterial) activity, or substantially no antimicrobial activity.

In the present invention, the treatment of CMTD includes the prevention, reduction or inhibition of the degeneration and/or pain associated with CMTD. For example, treatment is effective if it causes one or more of prevention/reduction/inhibition of: pain, discomfort, neural degeneration, progression of muscle atrophy/weakness, progression of sensory dysfunction, demyelination, associated with CMTD.

Preferably, the human is monitored during treatment. Monitoring is accomplished by observing a positive treatment result. After a positive result is observed, treatment is continued.

A concentration of a tetracycline compound having substantially no antibacterial activity is any concentration that does not significantly prevent the growth of bacteria. That is, a microbiologist would not consider the growth of bacteria to be inhibited from a clinical point of view. One way in which to quantify the antibacterial activities of tetracyclines is by a measure called minimum inhibitory concentration (MIC), as is known by a skilled artisan. An MIC is the minimum tetracycline concentration that inhibits the growth of a particular strain of bacteria in vitro. MIC values are determined using standard procedures. Standard procedures are, for example, based on a dilution method (broth or agar), or an equivalent, using standard concentrations of inoculum and tetracycline powder. See, for example, National Committee for Clinical Laboratory Standards. *Performance Standards for Antimicrobial Susceptibility Testing—Eleventh Informational Supplement*. NCCLS Document M100-S11, Vol. 21, No. 1, NCCLS, Wayne, PA, January, 2001.

In order to inhibit the growth of a strain of bacteria in vivo, a tetracycline compound achieves a plasma concentration in excess of the MIC for the strain. Plasma concentration refers to the concentration of a tetracycline compound measured in an individual's blood sample taken at steady state. Steady state is generally achieved after dosing for five to seven terminal half-lives. The half-lives of different tetracycline compounds vary from hours to days.

In the present invention, a tetracycline compound is administered in an amount that is effective, as described above, and that results in a plasma concentration which is significantly below the MIC for commonly-occurring bacteria. Such amounts are considered to have no, or substantially no, antibacterial activity. Examples of commonly-occurring bacteria that are susceptible to tetracyclines are *Escherichia coli* (e.g., ATCC 25922 and 25922); *Neisseria gonorrhoeae* (e.g., ATCC 49226); *Staphylococcus aureus* (e.g., ATCC 29213 and 25213); and *Streptococcus pneumoniae* (e.g., ATCC 49619).

For example, in the present invention, a tetracycline compound is administered in an amount that results in a plasma concentration which is less than approximately 80%, 75%, 70%, 65%, 60%, 55%, 50%, 45%, 40%, 35%, 30%, 25%, 20%, 15%, 10%, 5%, 1% or 0.5% of the MIC for the commonly-occurring bacteria mentioned above. A skilled artisan can readily determine the amount of a particular tetracycline compound to administer to achieve such concentrations.

For example, doxycycline is administered in an amount that results in a minimum steady state plasma concentration of about 0.1 μg/ml, 0.2 μg/ml, or 0.3 μg/ml, and a maximum steady state plasma concentration of about 0.7 μg/ml, 0.8 μg/ml, or 0.9 μg/ml.

The sub-antimicrobial amount of a tetracycline compound can also be expressed by daily dose. The daily dose of an antibacterial tetracycline compound is any amount that is sufficient to produce the effective, sub-antibacterial plasma concentrations described above. Such dose can, for example, be expressed as a percentage of a minimum antibacterial daily dose.

A skilled artisan knows, or is able routinely to determine, the minimum antibacterial daily dose for tetracycline compounds. Examples of suitable sub-antibacterial doses of antibacterial tetracycline compounds for the treatments described in the present specification include less than approximately: 80%, 75%, 70%, 65%, 60%, 55%, 50%, 45%, 40%, 35%, 30%, 25%, 20%, 15%, 10%, 5%, 1% and 0.5% of a minimum antibacterial dose.

Some examples of non-antibacterial daily doses of tetracycline compounds include about 20 mg/twice a day of doxycycline; about 38 mg of minocycline one, two, three or four times a day; and about 60 mg of tetracycline one, two, three or four times a day.

There is no necessary minimum effective amount of the tetracycline compound, as long as the amount administered is capable of providing the effective treatment. For example, when the amount is expressed as a percentage of the MIC plasma concentration, suitable minimum plasma concentrations include approximately 0.1%, 0.5%, 0.8% and 1% of the MIC plasma concentration. When the amount is expressed as a minimum actual plasma concentration, suitable actual plasma concentrations include approximately 0.01 μg/ml, 0.05 μg/ml, 0.1 μg/ml, 0.15 μg/ml, 0.2 μg/ml, 0.25 μg/ml and 0.3 μg/ml. When the dose is expressed as a percentage of a minimum antibacterial daily dose, the percentage is approximately 0.1%, 0.2%, 0.5%, 1%, 1.5% and 2% of the minimum antibacterial dose.

In a preferred embodiment, any form of doxycycline (e.g., doxycycline salts, such as doxycycline hyclate; and doxycycline hydrates, such as doxycycline monohydrate) is administered in a daily amount of, or equivalent to, from about 10 to about 60 milligrams of doxycycline, while maintaining a concentration in human plasma below the MIC.

In an especially preferred embodiment, doxycycline, a doxycycline salt, or a doxycycline hydrate, is administered at a dose of, or equivalent to, 20 milligrams of doxycycline twice daily. Such a formulation is sold for the treatment of periodontal disease under the trademark Periostat®.

Since CMTs have no, or substantially no, antibacterial activity, they can be administered at any effective dose at which side effects, if any, are acceptable. There is no risk of indiscriminate killing of bacteria, and the resulting threat of developing resistant bacteria.

For example, suitable maximum plasma concentrations of the CMTs described herein include about from about 50 μg/ml to about 400 μg/ml. Examples of other lower boundaries of this range include about 100 μg/ml, about 150 μg/ml and about 200 μg/ml. Examples of other upper boundaries of this range include about 250 μg/ml, about 300 μg/ml and about 350 μg/ml. Suitable daily doses of CMTs include about 1 mg/kg/day to about 200 mg/kg/day. Examples of other lower boundaries of this range include about 10 mg/kg/day, 18 mg/kg/day, about 40 mg/kg/day, and about 60 mg/kg/day. Examples of other upper boundaries of this range include about 70 mg/kg/day, about 80 mg/kg/day, about 100 mg/kg/day, and about 150 mg/kg/day, There is no necessary minimum effective dose of CMTs. Some typical minimum plasma concentrations of CMTs include, for example, about 0.01 μg/ml, 0.1 μg/ml, 0.8 μg/ml, and 1.0 μg/ml. Some typical minimum daily doses of CMTs include about 0.05 mg/day, about 0.1 mg/day, about 0.5 mg/day, about 1 mg/day, about 5 mg/day, or about 10 mg/day.

Examples daily doses of CMT-3 include doses of up to about 100 mg/day, about 80 mg/day, about 70 mg/day, 60 mg/day, about 50 mg/day, about 40 mg/day, about 30 mg/day, 20 mg/day, about 10 mg/day, about 5 mg/day, about 3 mg/day, about 2 mg/day, and about 1 mg/day. A dose of about 10 to about 20 mg/day of CMT-3 produces plasma concentrations in humans of about 1.0 μg/ml.

The actual preferred amounts of the tetracycline compounds (i.e., the antimicrobial tetracycline compounds or the CMT compounds) in a specified case will vary according to the particular compositions formulated, the mode of application, the particular sites of application, and the subject being treated (e.g., age, gender, size, tolerance to drug, etc.)

The tetracycline compounds may be administered at intervals. For example, the tetracycline compound may be administered 1-6 times a day, preferably 1-4 times a day.

The tetracycline compounds may be administered by controlled release. Controlled release administration is a method of drug delivery to achieve a certain level of the drug over a particular period of time. The level typically is measured by plasma concentration. Methods for controlled release of drugs are well known in the art.

In some embodiments, any of the doses of any of the tetracycline compounds are administered by controlled release over a 24 hour period. For example, CMT-3 is preferably administered in an amount of about 10 milligrams over the 24 hour period; and doxycycline is preferably administered in an amount of about 40 milligrams over the 24 hour period.

The tetracycline compounds can be in the form of pharmaceutically acceptable salts of the compounds. The term "pharmaceutically acceptable salt" refers to a salt prepared from a well-tolerated, nontoxic tetracycline compound and an acid or base. The acids may be inorganic or organic acids of tetracycline compounds. Examples of inorganic acids include hydrochloric, hydrobromic, nitric hydroiodic, sulfuric, and phosphoric acids. Examples of organic acids include carboxylic and sulfonic acids. The radical of the organic acids may be aliphatic or aromatic. Some examples of organic acids include formic, acetic, phenylacetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, alginic, tartaric, citric, gluconic, gulonic, arylsulfonic, and galacturonic acids. Appropriate organic bases may be selected, for example, from N,N-dibenzylethylene-diamine, chloroprocaine, choline, diethanolamine, ethylenediamine, meglumine (N-methylglucamine), and procaine.

The tetracycline compounds may be administered by methods known in the art. For example, the tetracycline compounds may be administered systemically. For the purposes of this specification, "systemic administration" means administration to a human by a method that causes the compounds to be absorbed into the bloodstream.

Preferably, the tetracycline compounds are administered orally by any method known in the art. For example, tetracyclines can be administered in the form of tablets, capsules, pills, troches, elixirs, suspensions, syrups, wafers, chewing gum and the like.

Additionally, the tetracycline compounds can be administered enterally or parenterally, e.g., intravenously; intramuscularly; subcutaneously, as injectable solutions or suspensions; intraperitoneally; or rectally. Administration can also be intranasally, in the form of, for example, an intranasal spray; or transdermally, in the form of, for example, a patch.

For the pharmaceutical purposes described above, the tetracycline compounds of the invention can be formulated per se in pharmaceutical preparations, optionally, with a suitable pharmaceutical carrier (vehicle) or excipient, as understood by practitioners in the art. These preparations can be made according to conventional chemical methods.

In the case of tablets for oral use, carriers commonly used include lactose and corn starch, and lubricating agents such as magnesium stearate are commonly added. For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums and glycols.

When aqueous suspensions are used for oral administration, emulsifying and/or suspending agents are commonly added. In addition, sweetening and/or flavoring agents may be added to the oral compositions.

For intramuscular, intraperitoneal, subcutaneous and intravenous use, sterile solutions of the tetracycline compounds can be employed, and the pH of the solutions can be suitably adjusted and buffered. For intravenous use, the total concentration of the solute(s) can be controlled in order to render the preparation isotonic.

The tetracycline compounds of the present invention can further comprise one or more pharmaceutically acceptable additional ingredient(s) such as alum, stabilizers, buffers, coloring agents, flavoring agents, and the like.

The tetracycline compounds are prepared by methods known in the art. For example, according to Mitscher (Mitscher in *The Chemistry of Tetracyclines*, Chapter 6, Marcel Dekker, Publishers, New York (1978)), the substituents at positions 5-9 of the tetracycline ring system may be modified without the complete loss of antibacterial properties. However, changes to the basic ring system or replacement of the substituents at positions 1-4 and 10-12 generally lead to synthetic tetracyclines with substantially less or effectively no antibacterial activity.

In one embodiment, the pharmaceutical composition comprises an active ingredient, wherein the active ingredient consists of: a tetracycline compound (i.e., a non-antimicrobial tetracycline compound, or antimicrobial tetracycline compound) and/or salt thereof.

In one embodiment, the pharmaceutical composition consists of (or consists essentially of): a tetracycline compound (i.e., a non-antimicrobial tetracycline compound, or antimicrobial tetracycline compound), and/or salt thereof; and at least one carrier and/or excipient.

In one embodiment, the pharmaceutical composition comprises an active ingredient which active ingredient consists essentially of a tetracycline compound (i.e., a non-antimicrobial tetracycline compound, or antimicrobial tetracycline compound). That is, any other ingredient(s) that may materially affect the basic and novel characteristics of the active ingredient of the invention are specifically excluded from the composition. Any ingredient which can potentially cause an undesirable effect/side effect, including, for example, an allergic response, may materially affect the basic and novel characteristics of the active ingredients of the invention.

The following are some examples of components which may materially affect the basic and novel characteristics of the active ingredient of the pharmaceutical compositions and may be excluded from certain embodiments of the present invention: creatine ligand; creatine monohydrate; dextrose, ceatine-ascorbyl derivative; 7-benzyl-4-(methylbenzyl)-2,4,6,7,8,9-hexahydroimidazo[1,2-A]pyrido[3,4-E]pyrimidin-5(1H)-one compounds (e.g., TIC10 or ONC201), and salts and derivatives thereof; small molecules with the functionality of inhibition of histone deacetylases; stanniocalcin compositions; albumin fusion proteins; ADAM polypeptides (i.e., a disintegrin and metalloprotease); a combination of tetracycline antibiotic/anti-fungal/statin; phthalazinedione; antibacterial tetracycline compounds; a bisphosphonate compound (including, for example, alendronate, clodronate, etidronate, pamidronate, risedronate, tiludronate, and zolendronate); and mechanistic target of rapamycin complex 1 (mTORC1) inhibitors, such as,

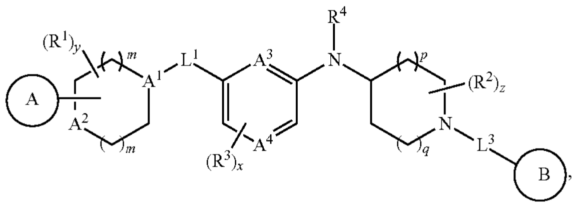

or a pharmaceutically acceptable salt thereof, wherein: $A^1$ is N or CH; $A^2$ is N(Ring A) or N—$R^1$; $A^3$ is C(R') or N; $A^4$ is CH or N; $R^1$ is H, $C_{1-6}$ aliphatic, or halogen; each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; each of m, n, p, q, and x is independently 0, 1, or 2; each of y and z is independently 0, 1, 2, 3 or 4; each of $R^1$ and $R^2$ is independently R, or: two $R^1$ groups are optionally taken together to form =O; two $R^2$ groups are optionally taken together to form =O; two $R^1$ groups are optionally taken together to form a covalent bond or a bivalent $C_{1-4}$ alkylene chain; or two $R^2$ groups are optionally taken together to form a covalent bond or a bivalent $C_{1-4}$ alkylene chain; an $R^1$ group and Ring A are optionally taken together with their intervening atoms to form a 5-8 membered fused ring having 0-2 heteroatoms independently selected from nitrogen, oxygen or sulfur; or an $R^2$ group and Ring B are optionally taken together with their intervening atoms to form a 5-8 membered fused ring having 0-2 heteroatoms independently selected from nitrogen, oxygen or sulfur; each of $R^3$ is independently R, halogen, —OR, —CN, or two $R^3$ groups are optionally taken together with their intervening atoms to form a 5-8 membered partially unsaturated or aryl fused ring having 0-2 heteroatoms independently selected from nitrogen, oxygen, or sulfur; $R^4$ is hydrogen or an optionally substituted $C_{1-6}$ aliphatic group; Ring A is absent or an optionally substituted ring selected from 6-membered aryl containing 0-2 nitrogen atoms, 5-membered heteroaryl with 1-4 heteroatoms independently selected from nitrogen, oxygen or sulfur, or 8-10 membered bicyclic aryl or heteroaryl with 1-4 heteroatoms independently selected from nitrogen, oxygen or sulfur; Ring B is an optionally substituted ring selected from 6-membered aryl containing 0-2 nitrogen atoms, 5-membered heteroaryl with 1-4 heteroatoms independently selected from nitrogen, oxygen or sulfur, or 8-10 membered bicyclic aryl or heteroaryl with 1-4 heteroatoms independently selected from nitrogen, oxygen or sulfur; and $L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, or —S(O)$_2$—.

The aforementioned ingredients may materially change the characteristics of the present pharmaceutical compositions due to unwanted effects and/or potential allergic responses. Examples of unwanted potential effects of creatine ligands and derivatives thereof include, for example, kidney damage/stones, liver damage, weight gain, bloating, dehydration, muscle cramps and digestive problems. Examples of unwanted potential effects of TIC10 include, for example, hair loss and immune compromise.

Example

The following example demonstrates that the Charcot Marie Tooth Disease symptoms are reduced or prevented when using the methods of the present invention.

A 47 year old man (hereinafter "the subject") had been diagnosed with Charcot Marie Tooth Disease at the age of 6 years old, and had suffered a variety of symptoms including neuropathic pain in his extremities, most notably in his toes. The subject described the pain during the daytime hours as a 2/10 and during the evening hours as a 6/10, and experienced this pain consistently for the prior 10 years.

The subject began taking a sub-antimicrobial dose of doxycycline, i.e., 20 mg twice daily (i.e. Periostat®). After approximately 2 weeks of continued twice-daily treatment with sub-antimicrobial dose doxycycline, with no substantive changes in any other aspect of the subject's treatment, diet, exercise or other activities, the subject experienced a dramatic reduction in neuropathic pain. Throughout the treatment period, the subject described the pain during daytime hours as a 1/10, and during the evening hours also as a 1/10. The subject continued twice-daily sub-antimicrobial dose doxycycline treatment for a period of 12 weeks, during which time he experienced no further change in neuropathic pain, and no adverse events were observed. Within 1 week of discontinuing twice-daily sub-antimicrobial dose doxycycline treatment, the subject experienced a return of the neuropathic pain in a sporadic manner.

Thus, while there have been described what are presently believed to be the preferred embodiments of the present invention, other and further embodiments, modifications, and improvements will be known to those skilled in the art, and it is intended to include all such further embodiments, modifications, and improvements as come within the true scope of the claims as set forth below.

TABLE 1

| | |
|---|---|
| CMT-1 | 4-dedimethylaminotetracycline |
| CMT-2 | tetracyclinonitrile |
| CMT-3 | 6-demethyl-6-deoxy-4-dedimethylaminotetracycline |
| CMT-301 | 7-bromo-6-demethyl-6-deoxy-4-dedimethylaminotetracycline |
| CMT-302 | 7-nitro-6-demethyl-6-deoxy-4-dedimethylaminotetracycline |
| CMT-303 | 9-nitro-6-demethyl-6-deoxy-4-dedimethylaminotetracycline |
| CMT-304 | 7-acetamido-6-demethyl-6-deoxy-4-dedimethylaminotetracycline |
| CMT-305 | 9-acetamido-6-demethyl-6-deoxy-4-dedimethylaminotetracycline |
| CMT-306 | 9-dimethylamino-6-demethyl-6-deoxy-4-dedimethylaminotetracycline |
| CMT-307 | 7-amino-6-demethyl-6-deoxy-4-dedimethylaminotetracycline |
| CMT-308 | 9-amino-6-demethyl-6-deoxy-4-dedimethylaminotetracycline |
| CMT-309 | 9-dimethylaminoacetamido-6-demethyl-6-deoxy-4-dedimethylaminotetracycline |
| CMT-310 | 7-dimethylamino-6-demethyl-6-deoxy-4-dedimethylaminotetracycline |
| CMT-311 | 9-palmitamide-6-demethyl-6-deoxy-4-dedimethylaminotetracycline |
| CMT-312 | 2-$CONHCH_2$-pyrrolidin-1-yl-6-demethyl-6-deoxy-4-dedimethylaminotetracycline |
| CMT-313 | 2-$CONHCH_2$-piperidin-1-yl-6-demethyl-6-deoxy-4-dedimethylaminotetracycline |
| CMT-314 | 2-$CONHCH_2$-morpholin-1-yl-6-demethyl-6-deoxy-4-dedimethylaminotetracycline |
| CMT-315 | 2-$CONHCH_2$-piperazin-1-yl-6-demethyl-6-deoxy-4-dedimethylaminotetracycline |
| CMT-4 | 7-chloro-4-dedimethylaminotetracycline |
| CMT-5 | tetracycline pyrazole |
| CMT-6 | 4-hydroxy-4-dedimethylaminotetracycline |
| CMT-7 | 4-dedimethylamino-12α-deoxytetracycline |
| CMT-8 | 4-dedimethylaminodoxycycline |
| CMT-801 | 9-acetamido-4-dedimethylaminodoxycycline |
| CMT-802 | 9-dimethylaminoacetamido-4-dedimethylaminodoxycycline |
| CMT-803 | 9-palmitamide-4-dedimethylaminodoxycycline |
| CMT-804 | 9-nitro-4-dedimethylaminodoxycycline |
| CMT-805 | 9-amino-4-dedimethylaminodoxycycline |
| CMT-806 | 9-dimethylamino-4-dedimethylaminodoxycycline |
| CMT-807 | 2-$CONHCH_2$-pyrrolidin-1-yl-4-dedimethylaminodoxycycline |
| CMT-808 | 2-$CONHCH_2$-piperidin-1-yl-4-dedimethylaminodoxycycline |
| CMT-809 | 2-$CONHCH_2$-piperazin-1-yl-4-dedimethylaminodoxycycline |
| CMT-9 | 4-de(dimethylamino)-12α-deoxyanhydrotetracycline |
| CMT-10 | 4-dedimethylaminominocycline (a.k.a. CMT-310) |
| CMT-1001 | 7-trimethylammonium-4-dedimethylaminosancycline |
| CMT-1002 | 9-nitro-4-dedimethylaminominocycline |

The invention claimed is:

1. A method of treating Charcot-Marie-Tooth Disease (CMTD) in a human in need thereof, the method comprising systemically administering to the human a non-antibacterial tetracycline compound in an amount that is effective to treat CMTD, wherein the non-antibacterial tetracycline compound is selected from the group consisting of: 6-demethyl-6-deoxy-4-dedimethylaminotetracycline (CMT-3); 4-dedimethylaminodoxycycline (CMT-8); 9-amino-6-demethyl-6-deoxy-4-dedimethylaminotetracycline (CMT-308); 4-de (dimethylamino)-minocycline (CMT-10), and salts thereof,
wherein creatine monohydrate and/or dextrose are/is not administered.

2. The method according to claim 1, wherein the non-antibacterial tetracycline compound is administered in an amount that results in a plasma concentration which is about 0.01 μg/ml to about 1 μg/ml.

3. The method according to claim 1, wherein the non-antibacterial tetracycline compound is administered at a daily dose of about 10 mg/kg/day to about 100 mg/kg/day.

4. The method according to claim 1, wherein the non-antibacterial tetracycline compound is administered at a daily dose of about 1 mg/kg/day to about 20 mg/kg/day.

5. The method according to claim 1, wherein the non-antibacterial tetracycline compound is administered by controlled release over a 24-hour period.

6. The method according to claim 1, wherein the systemic administration is oral administration or intravenous injection.

7. A method of treating Charcot-Marie-Tooth Disease (CMTD) in a human in need thereof, the method comprising systemically administering to the human a pharmaceutical composition comprising 6-demethyl-6-deoxy-4-dedimethylaminotetracycline (CMT-3) and salts thereof, in an amount that is effective to treat CMTD, wherein creatine monohydrate and/or dextrose are/is not administered.

8. The method according to claim 7, wherein CMT-3 is administered in an amount that results in a plasma concentration which is up to about 1.0 μg/ml.

9. The method according to claim 7, wherein CMT-3 is administered at a daily dose of up to about 1 to 20 mg/day.

10. A method of treating Charcot-Marie-Tooth Disease (CMTD) in a human in need thereof, the method comprising systemically administering to the human a pharmaceutical composition comprising 4-dedimethylaminodoxycycline (CMT-8) and salts thereof, in an amount that is effective to treat CMTD, wherein creatine monohydrate and/or dextrose are/is not administered.

11. A method of treating Charcot-Marie-Tooth Disease (CMTD) in a human in need thereof, the method comprising systemically administering to the human a pharmaceutical composition comprising 9-amino-6-demethyl-6-deoxy-4-dedimethylaminotetracycline (CMT-308) and salts thereof, in an amount that is effective to treat CMTD, wherein creatine monohydrate and/or dextrose are/is not administered.

12. A method of treating Charcot-Marie-Tooth Disease (CMTD) in a human in need thereof, the method comprising administering systemically to the human an antibacterial tetracycline compound in an amount that is effective to treat CMTD, but has no antibacterial activity, wherein the antibacterial tetracycline compound is doxycycline, minocycline, tetracycline, oxytetracycline, chlortetracycline, demeclocycline, lymecycline or pharmaceutically acceptable salts thereof, wherein creatine monohydrate and/or dextrose are/is not administered.

13. A method according to claim 12, wherein the antibacterial tetracycline compound is administered in an amount that results in a plasma concentration which is less than approximately 80%, 75%, 70%, 65%, 60%, 55%, 50%, 45%, 40%, 35%, 30%, 25%, 20%, 15%, 10%, 5%, 1% or 0.5% of MIC of the tetracycline compound for commonly occurring bacteria.

14. A method according to claim 12, wherein the antibacterial tetracycline compound is administered in an amount which is less than approximately 80%, 75%, 70%, 65%, 60%, 55%, 50%, 45%, 40%, 35%, 30%, 25%, 20%, 15%, 10%, 5%, 1% or 0.5% of the minimum antibacterial dose.

15. A method according to claim 12, wherein the tetracycline compound is doxycycline administered in a daily amount of from about 10 to about 60 milligrams.

16. A method according to claim 15, wherein the doxycycline is administered orally twice a day in a dose of about 20 mg.

17. A method according to claim 15, wherein the doxycycline is administered by controlled release over a 24 hour period, in an amount of about 40 milligrams.

18. A method according to claim 12, wherein the tetracycline compound is doxycycline administered in an amount which results in a plasma concentration in the range of about 0.1 to about 0.8 μg/ml.

* * * * *